Dec. 9, 1958 A. M. DANIELS Plant Pat. 1,777
APPLE TREE
Filed March 3, 1958
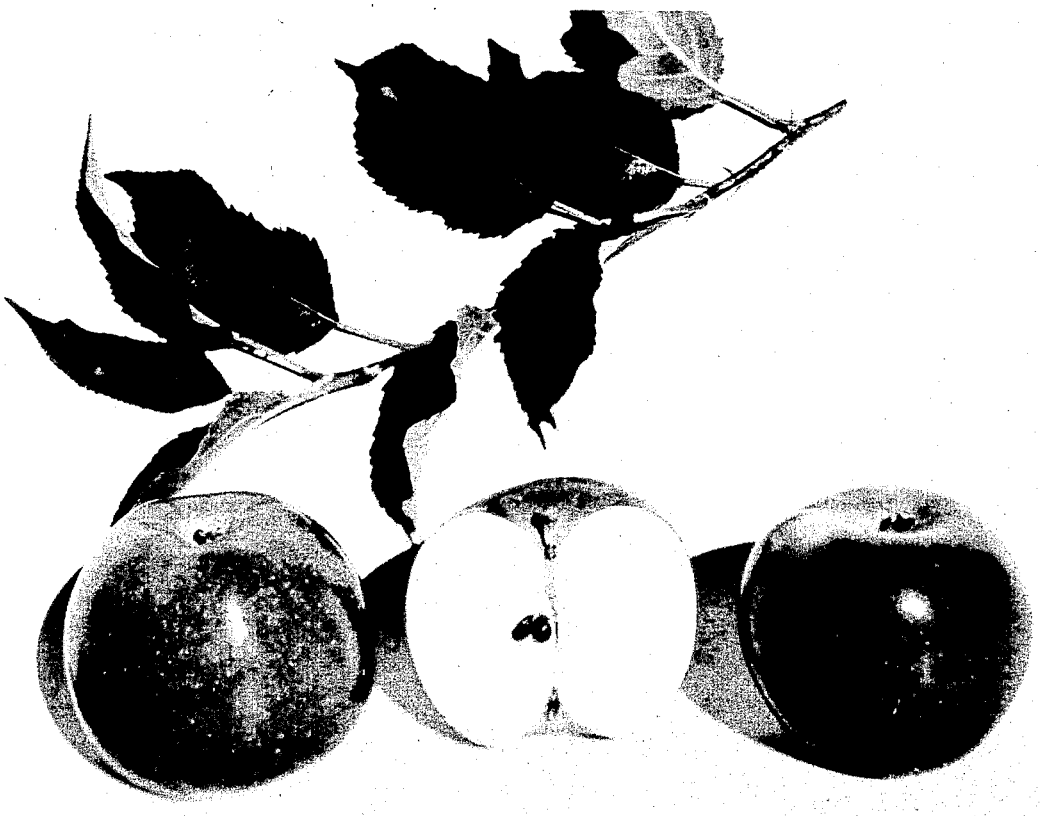
INVENTOR
A. M. Daniels
BY Robb & Robb
ATTORNEYS United States Patent Office Plant Pat. 1,777
Patented Dec. 9, 1958

1,777

APPLE TREE

Anna Morris Daniels, Abilene, Tex., assignor to Stark Bro's Nurseries and Orchards Company, Louisiana, Mo., a corporation of Missouri Application March 3, 1958, Serial No. 718,934

1 Claim. (Cl. 47—62)

The present invention relates to a new and distinct variety of apple tree which was discovered by me as a newly found seedling on my cultivated property in College Heights Addition of the city of Abilene, and county of Taylor, in the State of Texas.

At the time of my discovery, my attention was attracted to the new variety by the fact that it grew out from under or near the foundation of my home, and out of curiosity, I took steps to preserve the small originally-discovered plant, keep it under observation, and to later have it asexually reproduced on my behalf. These observations and asexual reproductions, as performed by grafting near Louisiana, Missouri, conclusively established that the new variety was characterized by an outstanding quality and appearance of its fruit.

More specifically, my new apple tree is particularly characterized as to novelty by the unique combination of good color, size, quality and flavor of the fruit, with a general resemblance of the fruit to that of the variety "Starking Delicious" (unpatented), but having a more globose form than the latter, a more acid flavor somewhat resembling that of the "Jonathan" (unpatented) variety, and an earlier maturity corresponding substantially to the ripening season to the "Jonathan" variety aforesaid, and approximately 6 days earlier than the ripening season of "Starking Delicious."

While the actual parentage of the new variety is not known, it is definitely differeniated from all other varieties of which I am aware, and is endowed with a unique and desirable combination of characteristics which is particularly valuable from a commercial standpoint and has heretofore never been available to the best of my knowledge.

The accompanying drawing shows typical specimens of the fruit and foliage of the new variety as depicted in color as nearly true as it is reasonably possible to make the same in a color illustration of this character, with one of the fruit specimens shown in cross-section.

The following is a detailed description of my new variety, with color terminology in accordance with Ridgway's Color Standards and Nomenclature (hereinafter abbreviated as "Ridgway"), and with the Horticultural Color Guide (hereinafter abbreviated as "HCG"), except where general color terms of ordinary dictionary significance are obvious:

(Observations made from specimens grown at Louisiana, Pike County, Missouri.)

Dates first and last pickings: From about September 5th to about September 12th; ripens about 6 days earlier than "Starking Delicious" and substantially simultaneously with "Jonathan."

Tree: Medium size; vigorous; upright; medium height; rapid-grower; hardy; productive; regular bearer.

*Trunk.*—Medium slender; smooth.

*Branches.*—Medium slender; little-branched. Color—Olive, Plate XXX—Color No. 21″—Tone M (Ridgway), with scarfskin Olive Gray, Plate LI—

Color No. 23″″″—Tone M (Ridgway). Lenticels—medium numerous; large.

*Leaves.*—Medium size; medium width; medium length; ovate; taper-pointed; medium thickness; rugose. Margin — coarsely serrate. Color — Spinach Green, Plate 0962, page 187, vol. 2 (HCG). Petiole—medium length; medium thickness.

Flowers: Medium late, as compared with other varieties; medium size.

*Date of first bloom.*—About April 25th.

*Date of last bloom.*—About April 29th.

*Color.*—White, with segments of lower side of petals Fuchsia Purple, Plate 28/2, page 28, vol. 1 (HCG).

Fruit:

*Maturity when described.*—Hard ripe (about September 10th).

*Size.*—Uniform. Axial diameter—about 2¾ inches. Transverse diameter—about 3¼ inches.

*Form.*—Globose; truncate at base and apex; slightly ribbed.

*Cavity.*—Symmetrical; rounded at base; flaring toward apex; undulate; pubescent toward apex. Depth — about 9/16 inch. Breadth — about 1¼ inches.

*Markings.*—Olive Ocher, Plate XXX—Color No. 21 (Ridgway).

*Basin.*—Unsymmetrical; rounded at base; wide; furrowed; crowned; pubescent. Depth—about 9/16 inch. Breadth—about 1¼ inches.

*Stem.*—Medium stout; pubescent; short. Length—about 9/16 inch. Breadth—about ⅛ inch.

*Calyx.*—From partly open to closed. Segments—persistent; narrowly lanceolate; acute; about 3/16 inch long; separated at base; erect; reflexed from base at apex; with outer and inner surfaces pubescent.

*Skin.*—Thick; tough; smooth; waxed. Dots—conspicuous; many large; even; ruptured; circular; color—Cartridge Buff, Plate XXX—Color No. 19″ (Ridgway). Ground color—Primrose Yellow, Plate 601/21, page 65, vol. 1 (HCG). Color markings—blushed; self-colored; bright; color—Cardinal Red, Plate 822/1, page 168, vol. 2 (HCG).

*Bloom.*—Wanting.

*Scarfskin.*—Wanting.

*General color effect.*—Bright solid red.

*Flesh.*—Juicy; satiny. Color—yellowish tinge. Texture—firm; tender; fine; crisp. Flavor—subacid. Aroma—distinct. Quality—best.

*Core.*—Median. Bundle area—medium size; oblate; acute at base. Halves of core—unequal. Bundles—inconspicuous; in one whorl; color—Chartreuse Green, Plate 663/2, page 90, vol. 1 (HCG). Core lines—meeting or slightly clasping; indistinct. Carpellary area—distinct; large. Calyx tube—pubescent toward base; broadly obconic; from cone shaped to funnel form, with short stem; depth about ¼ inch. Styles—present; fleshy at base; united toward base; pubescent throughout. Stamens—in one whorl; basal. Seed cells—axile; from closed to partly open; cell walls — thick; tough; length—about 11/16 inch; breadth—about ⅜ inch. Longitudinal section—broadly oval; obtuse at apex; surface fissured; cross-section narrow.

Seeds:

*Number.*—Usually 8 perfect; usually none imperfect; usually 2 per cell.

*Length.*—About 5/16 inch.

*Breadth.*—About 3/16 inch.

*Form.*—Obtuse.

*Color.*—Chestnut, Plate II—Color No. 9—Tone M (Ridgway).

Use: Market; dessert; culinary.

Keeping quality: Good; approximately 120 days in ordinary storage.

I claim:

A new and distinct variety of apple tree, substantially as herein shown and described, characterized particularly as to novelty by the unique combination of good color, size, quality and flavor of the fruit, with a general resemblance of the fruit to the variety "Starking Delicious," but differing therefrom by a more globose form, a more acid flavor somewhat resembling that of the variety "Jonathan," and an earlier maturity substantially corresponding to the ripening season of the "Jonathan" variety aforesaid.

No references cited.